US009114392B2

(12) United States Patent
Safar et al.

(10) Patent No.: US 9,114,392 B2
(45) Date of Patent: Aug. 25, 2015

(54) APPARATUS AND METHOD FOR HANDLING FLUIDS FOR ANALYSIS

(75) Inventors: Scott Safar, Burlington, WI (US); Stephen Herchenbach, Antioch, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 0 days.

(21) Appl. No.: 13/618,891

(22) Filed: Sep. 14, 2012

(65) Prior Publication Data

US 2013/0065315 A1    Mar. 14, 2013

Related U.S. Application Data

(62) Division of application No. 11/491,214, filed on Jul. 21, 2006, now Pat. No. 8,298,498, which is a division of application No. 10/360,956, filed on Feb. 7, 2003, now Pat. No. 7,125,722.

(60) Provisional application No. 60/393,827, filed on Jul. 3, 2002.

(51) Int. Cl.
*B01L 3/02* (2006.01)
*B01L 3/00* (2006.01)
(Continued)

(52) U.S. Cl.
CPC ............. *B01L 3/0234* (2013.01); *B01L 3/545* (2013.01); *B01L 9/06* (2013.01); *G01N 35/0099* (2013.01); *G01N 35/00732* (2013.01); *G01N 35/028* (2013.01); *G01N 35/1002* (2013.01); *G01N 35/1067* (2013.01); *B01J 2219/00585* (2013.01);
(Continued)

(58) Field of Classification Search
CPC ......... B01L 2200/16; B01L 9/06; B01L 9/52; G01N 35/1002; G01N 2035/00801; G01N 35/04; G01N 35/1011; G01N 35/1083; B01J 2219/00585
USPC ......... 422/62, 63, 65, 72, 297, 300, 400, 403, 422/430, 500, 560, 561, 562, 915, 939, 940, 422/941; 436/47
See application file for complete search history.

(56) References Cited

U.S. PATENT DOCUMENTS 4,193,983 A * 3/1980 Ullman et al. ................ 436/528
4,195,059 A   3/1980 Whitcher et al.
(Continued)

FOREIGN PATENT DOCUMENTS

DE    4113541 A1    11/1991
DE    4313807 C2     4/1993
(Continued)

OTHER PUBLICATIONS

"Streptococcal Grouping Identifies Lancefield Groups A, B, C, F, G and D Streptococci Within Minutes" [Online] XP002258649.
(Continued)

*Primary Examiner* — Dennis M White
(74) *Attorney, Agent, or Firm* — McDermott Will & Emery LLP

(57) ABSTRACT

An apparatus and method of loading reagent in a specimen handling device is disclosed. Fluids including specimen samples and reagents are moved between tubes during processing without directly passing over tubes which the reagents could contaminate. The apparatus may also include a head adapted to carry selected fluids in pipettes and a reagent receptacle adapted to permit entry of the head.

8 Claims, 8 Drawing Sheets

(51) Int. Cl.
  *B01L 9/06* (2006.01)
  *G01N 35/02* (2006.01)
  *G01N 35/04* (2006.01)
  *G01N 35/00* (2006.01)
  *G01N 35/10* (2006.01)

(52) U.S. Cl.
  CPC ...... *B01L 2200/021* (2013.01); *B01L 2200/025* (2013.01); *B01L 2200/0642* (2013.01); *B01L 2200/14* (2013.01); *B01L 2200/16* (2013.01); *B01L 2300/021* (2013.01); *G01N 35/04* (2013.01); *G01N 35/1011* (2013.01); *G01N 35/1083* (2013.01); *G01N 2035/00772* (2013.01); *G01N 2035/00801* (2013.01); *Y10T 436/11* (2015.01); *Y10T 436/113332* (2015.01); *Y10T 436/114165* (2015.01); *Y10T 436/2575* (2015.01)

(56) References Cited

U.S. PATENT DOCUMENTS

| | | | |
|---|---|---|---|
| 4,830,832 | A | 5/1989 | Arpagaus et al. |
| 4,935,875 | A | 6/1990 | Shah et al. |
| 5,122,342 | A | 6/1992 | McCulloch et al. |
| 5,316,726 | A | 5/1994 | Babson et al. |
| 5,358,691 | A * | 10/1994 | Clark et al. ............ 422/64 |
| 5,417,922 | A | 5/1995 | Markin et al. |
| 5,420,408 | A | 5/1995 | Weyrauch et al. |
| 5,482,861 | A | 1/1996 | Clark et al. |
| 5,591,642 | A | 1/1997 | Jones |
| 5,597,733 | A | 1/1997 | Bell et al. |
| 5,663,545 | A | 9/1997 | Marquiss |
| 5,788,928 | A | 8/1998 | Carey et al. |
| 5,795,784 | A | 8/1998 | Arnquist et al. |
| 5,948,359 | A | 9/1999 | Kalra et al. |
| 6,060,022 | A | 5/2000 | Pang et al. |
| 6,066,300 | A | 5/2000 | Carey et al. |
| 6,335,166 | B1 | 1/2002 | Ammann et al. |
| 6,413,780 | B1 | 7/2002 | Bach et al. |
| 6,982,063 | B2 | 1/2006 | Hamel et al. |
| 2002/0012916 | A1* | 1/2002 | Gundling et al. ............ 435/6 |
| 2002/0034456 | A1 | 3/2002 | Ford et al. |

FOREIGN PATENT DOCUMENTS

| | | |
|---|---|---|
| DE | 19962689 A1 | 7/2001 |
| EP | 0226867 A2 | 7/1987 |
| EP | 0325101 B1 | 3/1993 |
| EP | 0738541 B1 | 1/2002 |
| JP | 55-143566 | 10/1980 |
| JP | 08-271525 A | 10/1996 |
| JP | 08-292194 A | 11/1996 |
| JP | 09-211004 A | 8/1997 |
| JP | 10-109429 A | 4/1998 |
| JP | 2000-346851 A | 12/2000 |
| JP | 2002-055111 A | 2/2002 |
| WO | 87/05533 A1 | 9/1987 |
| WO | 99/57561 A3 | 11/1999 |
| WO | 99/66334 A1 | 12/1999 |
| WO | 00-21668 A1 | 4/2000 |
| WO | 01/20532 A2 | 3/2001 |
| WO | 02/39084 A2 | 5/2002 |

OTHER PUBLICATIONS

"A Sensitive Rapid Strep A Test" Stanbio Laboratory [Online] XP002258650.

Environment Directorate, OECD: "OECD Principles on Good Laboratory Practice" OECD Series on Principles of Good Laboratory Practice and Compliance Monitoring [Online] No. 1, Jan. 26, 1998, pp. 1-41, XP002558651.

"Environment Directorate, OECD: OECD Principles on Good Laboratory Practice," OECD Series on Principles of Good Laboratory Practice and Compliance Monitoring, Internet Citation, Feb. 16, 1998, XP 002258651.

English Translation of Office Action for Japanese Patent App. No. 2004-519790 dated Feb. 10, 2009.

"PCR Reagents," Abgene 2001/2002 Catalogue Emerging Technologies in Life Sciences, 2001, Epsom, Surrey, UK, XP002591219, pp. 8-25.

International Search Report for PCT/US03/020877 dated Feb. 18, 2004.

European Search Report for EP App. No. 05 00 8927, Published as EP 1577675, dated Oct. 6, 2006.

European Search Report for EP App. No. 09 17 2792, Published as EP 2143494, dated Dec. 3, 2009.

European Search Report for EP App No. 10 16 3856, Published as EP 2223745, dated Jul. 9, 2010.

English Translation of Official Action/Notice of Rejection from the Japanese Patent Office for Japanese Patent Application No. 2009-188227, mailed Sep. 27, 2011.

* cited by examiner

APPARATUS AND METHOD FOR HANDLING FLUIDS FOR ANALYSIS

RELATED APPLICATION DATA

This application is a divisional application of U.S. Utility patent application Ser. No. 11/491,214, filed Jul. 21, 2006, now U.S. Pat. No. 8,298,498, which is a divisional application of U.S. Utility patent application Ser. No. 10/360,956, filed Feb. 7, 2003, now U.S. Pat. No. 7,125,722, which claims priority in U.S. Provisional Patent Application Ser. No. 60/393,827, filed Jul. 3, 2002, all three of which are entitled "Apparatus and Method for Handling Fluids for Analysis". The full disclosure of these applications are hereby incorporated by reference.

BACKGROUND OF THE INVENTION

The present invention is directed toward testing of specimens, and particularly toward an apparatus and method for properly adding fluids such as reagents during the processing of specimens for testing.

Testing sample biological specimens is commonly done, for example, to check for the presence of an item of interest, which item may be or include all or portions of a specific region of DNA, RNA, or fragments thereof, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, functional equivalents of the above, etc. Specimens such as a patient's body fluids (e.g., serum, whole blood, urine, swabs, plasma, cerebra-spinal fluid, lymph fluids, tissue solids) can be analyzed using a number of different tests to provide information about a patient's health.

In such testing, it is imperative that the specimens be handled in a manner which prevents contaminants from being introduced to the specimens, whether from the outside environment or between specimens. For example, where the HIV virus from one specimen is inadvertently allowed to contaminate the specimen of a different patient, the resulting false positive test result could potentially have catastrophic psychological effect on the patient, even should subsequent testing later discover the error. Moreover, since such testing is highly sensitive, even the smallest amounts of contamination can cause erroneous test results. Simply put, it is imperative that the specimens be properly handled.

In such sophisticated testing, it is also imperative that the various reagents which may be used in the testing be properly handled as well, not only to avoid contaminants but also to ensure that the proper reagent in proper quantities is used at appropriate times.

Commonly, such testing is accomplished using automated devices which handle multiple specimens and fluids (typically, reagents). Such automated devices typically will use sets of pipettes to move various fluids between their original containers (usually receptacles such as open topped tubes) and containers in which the specimens are to be processed. For example, a set of 8 specimens may be contained in 8 tubes or other receptacles loaded in a rack on the device, and a head carrying 8 pipettes will through programmed motion move the pipettes into those 8 tubes, where a vacuum will be applied to extract a selected amount of each specimen from its tube into the pipettes. The head will then retract the pipettes from the tubes and move over to another set of tubes located at a processing station, depositing the extracted amounts of each specimen from the pipettes into sets of testing tubes.

At the processing station of such automated devices, the specimens are variously handled according to the purpose of the testing (e.g., incubated, prepared, lysed, eluted, analyzed, read, etc.). For example, the specimens may be prepared for analyzing, as for example by separating DNA or RNA from the specimen. The specimens may also or alternatively be analyzed. Commonly, such processes involve the addition of various fluids (typically reagents) to the specimen in each tube. For example, in a first step, a reagent may be added to each of the tubes to wash the specimens, and second and third (and more) reagents may be added to the specimens in the course of carrying out other processes to, for example, unbind and/or separate the DNA or RNA of interest allow so that it may be extracted from the specimen in each tube for subsequent testing. Similar processes, in which the same or different reagents are added to the tubes, may also occur after the specimen has been prepared as a part of the analyzing of the prepared specimens.

The handling of the reagents and other fluids can, with such automated devices, be problematic. Though the reagents may be automatically moved from receptacles to the specimen containing tubes in the processing station by use of the head and pipettes such as noted, it is in the first instance necessary to load the appropriate reagent into the appropriate receptacle on the device in order to ensure that the head and pipettes are adding the appropriate reagent to the appropriate specimen containing tube at the appropriate time in the process. Further, it should be recognized that it is necessary for the receptacles to be readily cleaned, whether to remove possible contaminants or to permit use of different fluids in connection with different processes. As a result of such requirements, the receptacles are typically readily removable from the apparatus for such action.

Heretofore, loading the appropriate reagent into the appropriate receptacle has been accomplished in several different ways. In one such procedure, the individual who is controlling the device manually measures and adds the reagents to receptacles, and then places those receptacles on the device. In another such procedure, the loading of reagents is automatically accomplished by the device itself, which uses some transfer apparatus (such as a head and pipette(s) as previously described) to move the reagents from bulk supplies of the reagents provided with the device.

However, as already noted, either of the above procedures can be problematic. For example, manually adding the reagents can introduce human error, whether erroneously preparing the reagent, adding reagents to the wrong receptacles, or even mounting the receptacle incorrectly on the device. In the latter case, even if the correct reagents are loaded in the correct amounts, they will be at the wrong location on the device so that when the head and pipettes automatically draw a reagent for use at a certain step of the processing, it may well be the wrong reagent, or there could be no reagent of any kind where the head and pipettes go to extract it. Further, while such errors may be reduced using the second procedure (in which the device itself loads reagents from bulk supplies), the bulk supplies can themselves take up more room than is desirable for the device. Further, allowing this process to be accomplished by the device will, naturally, tie up the device while it carries out those steps. Tying up the device can reduce the amount of tests which are performed during a given day, and thereby either delay the completion of tests or require significant additional investment of capital for additional devices to allow for a desired testing capacity level.

The present invention is directed to overcoming one or more of the problems as set forth above.

SUMMARY OF THE INVENTION

In one aspect of the present invention, a specimen handling device is provided, including a deck with a plurality of positions defined thereon, a plurality of trays each of which is removably securable to only a specific one of the positions on the deck, and at least one reagent receptacle on each of the plurality of trays, where each of the reagent receptacles is adapted to contain a selected reagent.

In one form of this aspect, mating pairs of mounting members are provided on the trays and the deck, respectively, wherein the mounting member on each tray mates with only one of the mounting members on the deck, and the mounting member on the deck is at the specific one of the positions on the deck to which the tray with the mating mounting member is removably securable.

In another aspect of the invention, a specimen handling device is provided, including a deck with a plurality of positions defined thereon, a plurality of trays, each of which is removably securable to a specific one of the positions on the deck and includes an optically readable identifier, and at least one reagent receptacle on each of the plurality of trays with each receptacles adapted to contain a selected reagent.

In one form of this aspect of the invention, each optically readable identifier is a distinct one of a first set of icons, and each distinct one of the first set of icons also visually marks the specific one of the positions on the deck to which the tray including the distinct one of the first set of icons is removably securable.

In another form of this aspect of the invention, each optically readable identifier is a distinct bar code, with a bar code reader adapted to read the bar code on the trays when secured to one of the positions, and a controller for the specimen handling device indicating an error if the bar code reader reads a bar code on a tray at a specific one of the positions which is not associated with the tray securable to the specific position.

In yet another aspect of the present invention, a specimen handling device is provided with a deck with a plurality of positions defined thereon and each of the positions is visually marked by a distinct one of a first set of icons, and a plurality of trays, each of which is removably securable to a selected one of the positions on the deck and includes the distinct one of the first set of icons visually marking the selected one of the positions. At least one reagent receptacle is on each of the plurality of trays, with each of the reagent receptacles being visually marked by a distinct one of a second set of icons. A kit is also provided including a plurality of containers with selected reagents therein, each of the containers being visually marked by the distinct one of the second set of icons visually marking a selected one of the reagent receptacles in which the selected reagent in the container is to be poured.

In one form of this aspect of the invention, the specimen handling device is capable of handling Z specimens and the kit includes S subsets of containers, where each subset contains each of the selected reagents in a quantity sufficient for use with a selected number X of specimens, where X substantially equals Z/S. At least 2 of the reagent receptacles are incapable of holding at least one of the selected reagents in a quantity sufficient for use with Z specimens, and graphic indicators are provided on the at least 2 of the reagent receptacles to indicate into which of the reagent receptacles to pour the container of the at least one of the selected reagents from a first subset of containers where at least 1 specimen is being handled, and indicating into which of the reagent receptacles to pour the container of the at least one of the selected reagents from a second subset of containers where at least X+1 specimens are being handled, and indicating into which of the reagent receptacles to pour the container of the at least one of the selected reagents from a S subset of containers where at least [(S−1)*X]+1 specimens are being handled.

In still another aspect of the present invention, a specimen handling device is provided including a deck having a plurality of positions defined thereon with a plurality of open top receptacles with reagents therein, a head adapted to carry selected fluids in X pipettes over the deck, X being 3 or more and the pipettes being arranged in a row with a uniform spacing therebetween, racks on the deck for supporting individual open top tubes in groups of X with the racks supporting the tubes in each group with the uniform spacing, and a controller controlling the head to move a selected one of the reagents in the pipettes from the receptacle containing the selected one of the reagents to a selected group of the tubes whereby the head passes over groups of the tubes other than the selected group of the tubes with the pipettes above and between the tubes of the other groups of tubes.

In a still further aspect of the present invention, a specimen handling system is provided including an instrument and a reagent kit. The instrument includes a head adapted to carry selected fluids in X pipettes, a reagent receptacle adapted to permit entry of the head and fillable by manual pouring of reagents into the receptacle, and a holder for an array of reaction vessels for receiving specimens. The reagent kit includes a container with a premeasured quantity of particles in a premeasured volume of fluid, wherein the particles have affinity for biological analytes of interest, and the container is adapted for pouring into the reagent receptacle.

In yet another aspect of the present invention, the above specimen handling system may be employed in a method of detecting a biological analyte of interest in which an internal control analyte is added to the contents of the container prior to pouring the contents of the container into the reagent receptacle.

DETAILED DESCRIPTION OF THE INVENTION

Figure 1:
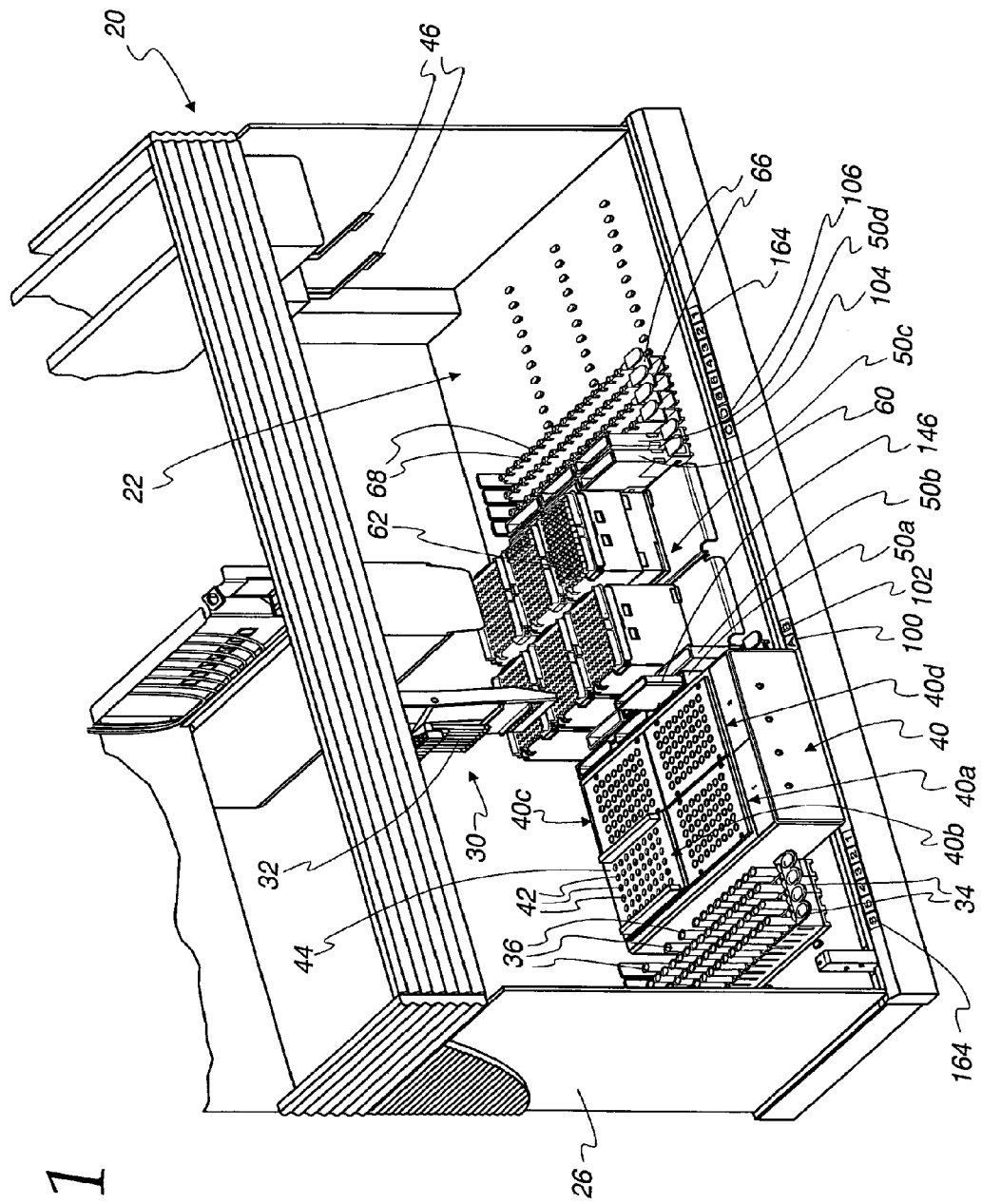
FIG. 1 is a perspective partial view of an automated testing device incorporating the present invention.
Figure 2:
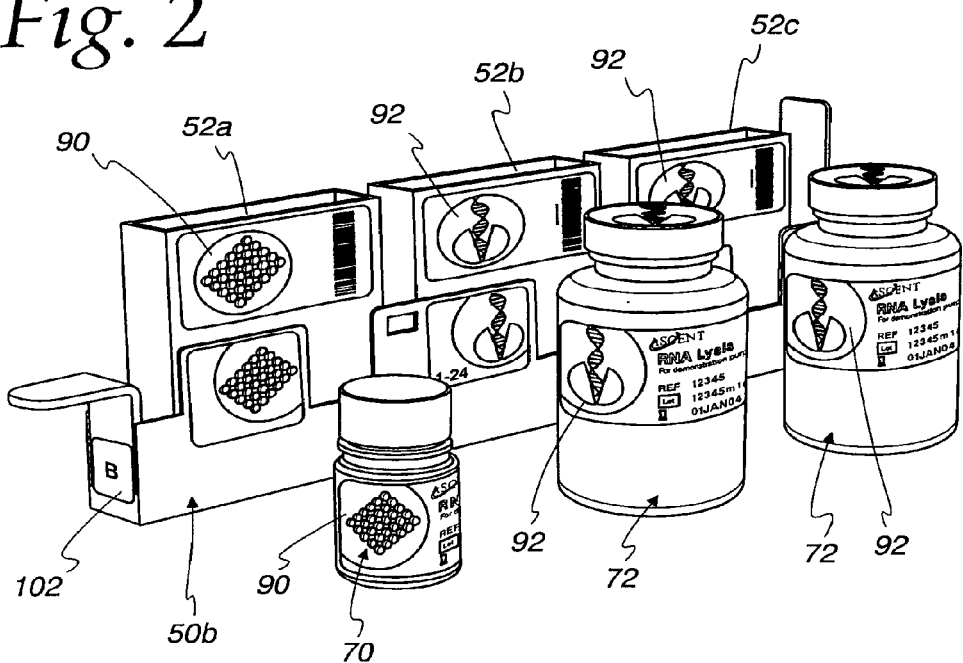
FIGS. 2-5 are perspective views of reagent containers and trays used with the testing device of FIG. 1.
Figure 3:
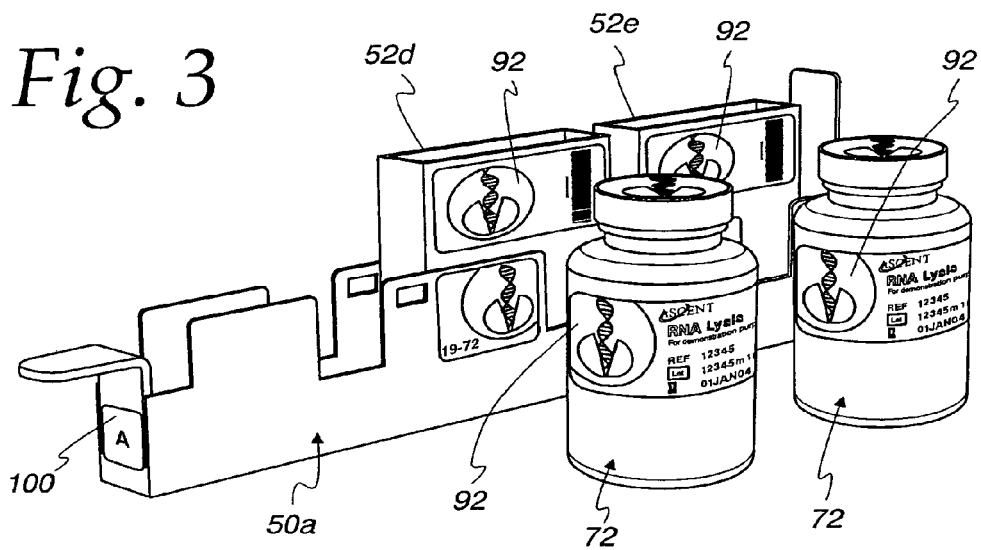
Figure 4:
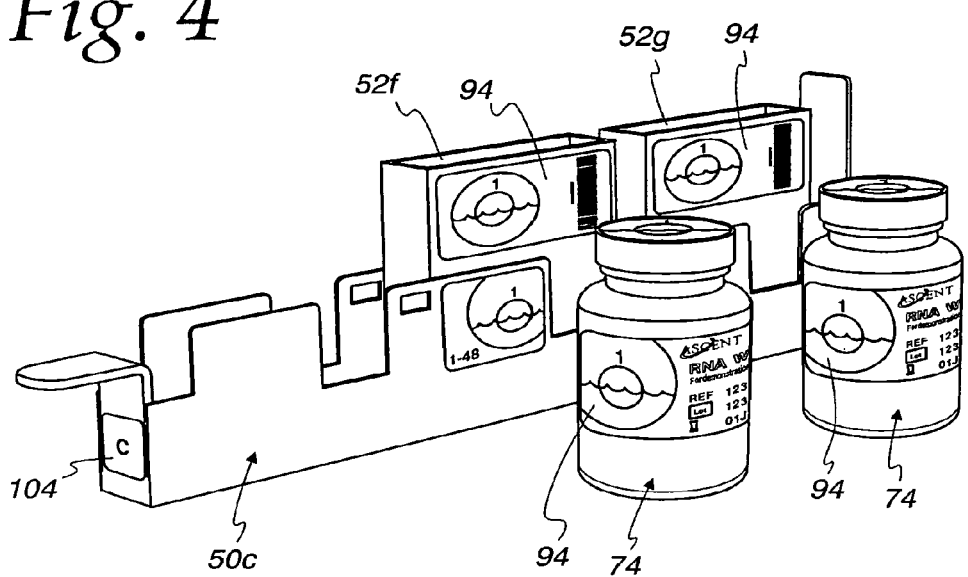
Figure 5:
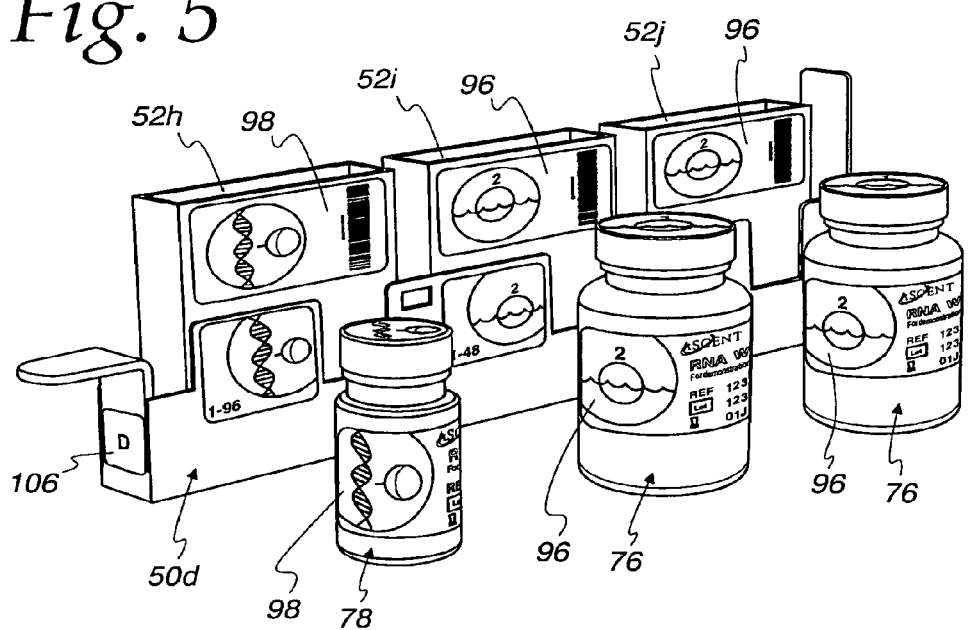

An automated testing device 20 incorporating the invention described herein is illustrated in FIG. 1. For simplicity of explanation of the invention, many of the components of the testing device 20 are not (and need not be) shown in the figures. The automatic testing device may be adapted for the substantial isolation of nucleic acids from biological samples, including the isolation and testing of nucleic acids from biological samples. In that context, FIG. 1 generally illustrates a deck 22 of the testing device 20 on which testing of specimen samples may be done. In the testing device 20 as discussed herein, specimens may be loaded onto the deck 22 of the device 20 along with other items necessary for the desired test, such as reagents and pipettes. A hood 26 is also generally shown in FIG. 1 to protect against contamination from the environment in which the device 20 is located. The hood 26 may be any suitable enclosure for preventing outside contaminants from entering therein as is known in the art, and the particular hood 26 used is not significant to the present invention except insofar as it may be opened to allow the device operator access to the deck 22 as is common. Although not shown, the automatic testing device may advantageously also include one or more of the following features: (1) two heating elements, each capable of controllably heating volumes of up to 168 milliliters (48 tubes×3.5 milliliters per tube) to at least 50° C. and more preferably at least 75° C., (2) a receptacle to hold and segregate from samples and reagents used pipette tips such that contamination from used tips is minimized, (3) aerosol control devices, for example without limitation, (a) a sample tube or reagent tube sealer, (b) electrodes for treating surfaces and/or liquids with electrical current capable of modifying nucleic acids, (c) an ultraviolet light source capable of degrading or modifying nucleic acids, (d) an apparatus for causing laminar air flow in or around the automatic testing device, (4) a temperature controller capable of cycling temperatures of samples and/or reagents in a manner suitable for PCR, (5) magnets for use in combination with a pipettor or other aspiration system capable of substantially separating magnetic particles from liquids in which they may be suspended, and (6) an optical detector (e.g., a flourometer) for measuring the light absorbance or fluorescence of processed samples.

Inside the hood 26 and disposed above the deck 22 is a head 30 including a linear array of pipettors 32 suitably adapted to releasably secure disposable pipettes thereto as is known. The array of pipettors 32 may advantageously be arranged in a selected uniform spacing for purposes which will become apparent. Moreover, the head 30 may suitably support the pipettors 32 so that the uniform spacing therebetween may be selectively adjusted. A suitable drive and controller is provided with the device 20 to control movement of the head 30 and pipettors 32.

Suitable racks 34 are provided for supporting tubes 36 with specimens therein, with the racks 34 being removably secured to the deck 22 such as further detailed hereafter.

A processing station 40 is located on the deck 22, at which specimen samples may be processed. In the present description, the processing is to isolate an analyte of interest from the specimen (e.g., DNA or RNA), after which processing the isolated analyte may be further tested according to an appropriate protocol. However, it should be understood that the present invention is not limited in any way to such processing, and could as easily be used with a device in which different processing or protocols are carried out.

In the disclosed embodiment, the processing station 40 includes four stations 40a-d, where samples of the specimens from the tubes 36 in the racks 34 may be processed according to testing requirements. Test tubes or reaction vessels 42 in a support bracket 44 may be suitably moved between the stations 40a-d, for example by transfer arms 46 suitably controlled and driven to pick up and move the support bracket in the hood 26 as desired. For example, while the bracket 44 is shown at station 40b in FIG. 1, during the initiation of the processing, the bracket 44 may be at station 40a, where specimen samples are initially loaded into supported test tubes 42. As described in more detail below, some processing may occur at station 40a, such as washing the specimen samples, after which the transfer arms 46 move the support bracket 44 to a second station 40b, where different processing (e.g., lysis) may occur. Different conditions may be provided at different stations 40a-d (e.g., heating, cooling, magnetic fields) according to the protocols for the processing being done. As also described in more detail hereafter, different reagents may be introduced to the test tubes 42 at each station.

While different reagents may be used within the scope of the invention (with the reagents being principally dependent on the desired processing of the specimen samples), where the processing is sample preparation in which a particular biological item of interest is to be analyzed, the reagent may advantageously include particles having an affinity for those biological analytes of interest. Particles having affinity for biological analytes of interest that are useful in the context of the present invention include, without limitation, particles having glass, silica or metal oxide surfaces. Similarly, the automatic testing device may be constructed so as to resist the corrosive effects of strong bases (e.g., potassium hydroxide) and reagents comprising high concentrations of chaotropes commonly used in the isolation of nucleic acids (e.g. 4.5 M (or higher) guanidinium isothiocyanate or 5 M (or higher) urea.

A plurality of trays 50a-d having receptacles 52 for different reagents are also provided, with the trays 50a-d being removably secured to the deck 22 such as further detailed hereafter. Further, a pipette supply station 60 is also secured to the deck 22, with the pipette supply station 60 being loaded with supplies of different sized and disposable pipettes 62 for use by the device 20.

Racks 66 supporting tubes 68 for processed specimen samples are also removably securable to the deck 22. In the illustrated embodiment, for example, DNA isolated at the processing station 40 may be removed from the test tubes 42 and transferred by the head 30, pipettors 32 and suitable pipettes 62 to the tubes 68 in racks 66. Further processing of the isolated DNA may then be separately done according to protocol appropriate for analyzing, for example, a specific region of the DNA. Additional equipment may be included in the device 20 if necessary for such protocol. Again, it should be noted that the present invention may be used with virtually any type of processing, in particular where different fluids such as reagents are used in the processing. The racks 66 may be releasably secured to the deck 22 to allow washing and decontamination of the racks 66.

FIGS. 2-5 illustrate the four trays 50a-d together with pre-mixed and measured containers or packages 70, 72, 74, 76, 78. The containers 70-78 are provided in a kit 80 (see FIG. 6) which, in the illustrated embodiment, contain five different containers 70-78 all for use in processing a specific number of specimen samples, with the kit 80 having four groups of those containers 70-78.

Figure 6:
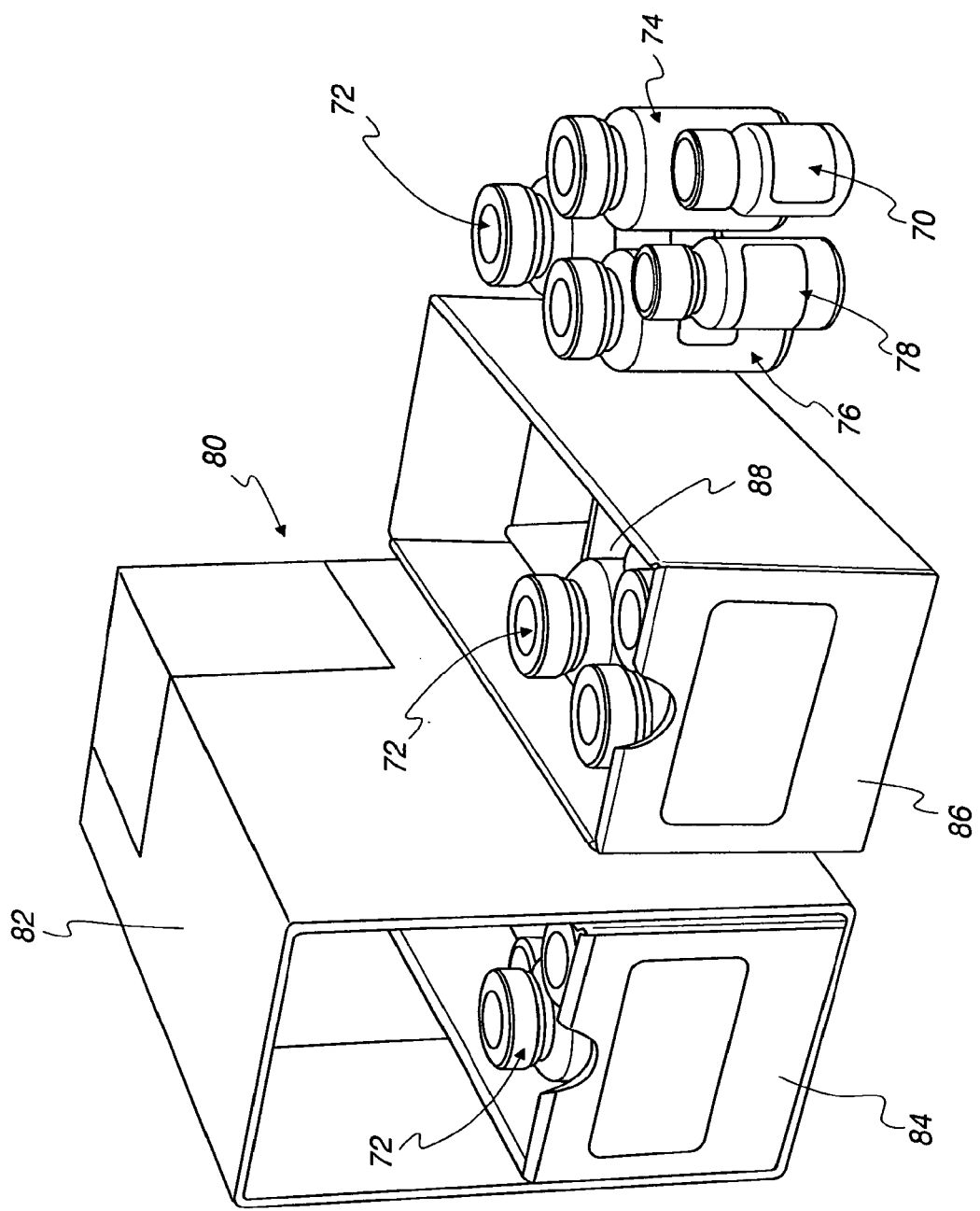
FIG. 6 is a perspective view of a reagent kit usable with the trays of FIGS. 2-5.

The kit 80 may be packaged in any suitable manner, including that illustrated in FIG. 6 in which a single box 82 is provided with two boxes 84, 86 therein, with each interior box 84, 86 including a divider 88 therein separating two different groups of containers 70-78. The kit can optionally also contain instructions relating to the use of the kit for the preparation of nucleic acids and/or the use of such prepared nucleic acids in diagnosing a disease or condition.

In the illustrated embodiment, as an example, it should be appreciated that up to ninety-six specimens may be processed at one time. Thus, the test tubes 36 are arranged in six rows of eight by the support bracket 44, where two different support brackets 44 may be used and shifted between different stations at one time. Similarly, up to four racks 34 may each support twenty-four tubes 36 of specimens in a row, as may up to four racks 66 each support twenty-four tubes 68 for the processed specimen samples. Each of the four groups of containers 70-78 in the kit 80 contain measured amounts of reagents required for processing twenty-four specimen samples. While such numbers of specimens and quantities are convenient (e.g., a head 30 carrying eight pipettes 62 can conveniently move quantities of samples and reagents between such arrays of tubes), it should be understood that the present invention is clearly not limited to a device 20 in which such arrays in such numbers are used.

Referring again to FIGS. 2-5, it can be seen that each tray 50*a-d* includes open topped receptacles 52*a-j* which are marked by icons 90, 92, 94, 96, 98 representative of a particular reagent to be used in the processing. For example, icons 94 and 96 may represent a wash fluid. However, the particular graphical representation included in the icon 90-98 can be anything, including numerals or letters or other symbols, colors or combinations thereof, with the important aspect being that the icon used on a particular receptacle 52 match the icon on the container 70-78 containing the reagent to be poured therein.

Further, the receptacles 52*a-j* may be marked with an indication of how many reagent containers 70-78 from the kit 80 should be poured into the receptacle depending on the number of specimen samples being processed. For example, it will be understood by the operator that one group of containers 70-78 should be used if 1-24 samples are to be processed, two groups if 25-48 samples are to be processed, three groups if 49-72 samples are to be processed, and all four groups if 73-96 samples are to be processed.

Where the receptacle 80-88 for a given reagent is adequate in size to hold all of the reagent needed even for full testing (e.g., for ninety-six samples), then the appropriate number of such containers 70-78 should be poured into that receptacle 52*a-j* depending on the number of samples being tested. For reagents which are used in smaller relative quantities, such as the reagents in containers 70 (FIG. 2) and 78 (FIG. 5), all of each reagent may be poured into one receptacle. Thus, when processing a full capacity of ninety-six samples, four containers 70, 78 respectively of those reagents would be poured into the receptacles 52*a*, 52*h* marked with the corresponding icon 90, 98. As another example, when processing only 25-48 samples, only two containers 70, 78 of each such reagent would be added to the respective receptacles 52*a*, 52*h*.

Where a larger quantity of a particular reagent is used than can be held by a particular receptacle 52, then multiple receptacles 52*b-g*, 52*i-j* are used for that reagent, with a mark provided on the receptacles 52*b-g*, 52*i-j* to indicate which to fill based on the number of samples being processed. Thus, for example, referring to FIGS. 2-3 where it can be seen that relatively larger quantities of the reagent of container 72 would be used, one container 72 would be poured into receptacle 52*b* (marked with "1-24") for processing of 1-24 samples, a second container 72 would additionally be poured into receptacle 52*c* (marked with "25-48", though not seen in the Figure) for processing of 25-48 samples, a third container 72 would additionally be poured into receptacle 52*d* (marked with "49-72") for processing of 49-72 samples, and a fourth container 72 would additionally be poured into receptacle 52*e* (marked with "73-96", though not seen in the Figure) for processing of 73-96 samples. Such a marking thus helps to ensure that appropriate reagent is used when less than 73 (in the present example) samples are being processed (e.g., the head 30 will be controlled to go to only receptacles 52*b-d* for 72 samples, and an error would occur if one of the three containers 72 with that reagent were poured into receptacle 52*e*, leaving one of receptacles 52*b-d* empty).

Similarly, for reagents used in intermediate amounts (such as in containers 74 and 76), two receptacles (52*f-g* and 52*i-j*, respectively) may be used, with the first two containers (74 or 76) of a particular reagent being poured into a first receptacle marked with "1-48" (52*f* or 52*i*, respectively), and additional containers of that reagent poured into a second receptacle (52*g* or 52*j*, respectively) marked "49-96" where more than 48 samples are being processed. Alternate methods of pouring quantities of a particular reagent into multiple receptacles would, however, be within the scope of the invention.

It can thus be appreciated that through the use of the kit 80 and trays 50*a-d* with receptacles 52*a-j* and icons 90-98, an individual operator of the device 20 may readily and reliably provide the proper amount and mixture of reagents for use by the machine, with minimal risk of operator error in doing so. Further, this operation may also be accomplished without requiring that the device itself be programmed to do so, be tied up in doing so, or be required to hold bulk quantities in doing so. Further, the use of such prepared reagents in specific containers 70-78 readily allows for a preselected quantity of internal control particles to be precisely and reliably added to the reagents to advantageously allow for a later estimation of how efficiently the analyte of interest (e.g., DNA) is isolated by the processing. Such internal control particles may be easily measured in a known specific quantity for use with the known standard quantity of reagent in the particular container 70-78, so that an appropriate fluid mix may be provided for the desired sample processing.

As also shown in FIGS. 2-5, in addition to the use of icons 90-98 to ensure that the proper quantities of the proper reagents are used for processing, a second set of icons 100, 102, 104, 106 are also used on the end of the trays 50*a-d* in conjunction with matching icons 100-106 on the deck 22 to ensure that the operator can easily and reliably locate each tray 50*a-d* at the proper location on the deck 22. These icons 100-106, too, can be anything, including numerals or letters or other symbols, colors or combinations thereof. This use of these icons 100-106 thus further ensures that the trays 50*a-d* and receptacles 52*a-j* are properly positioned on the deck 22, so that the head 30 will pick up the proper reagents when it proceeds according to its programmed operation to a particular location at which the receptacle for that reagent is supposed to be located.

Figure 7:
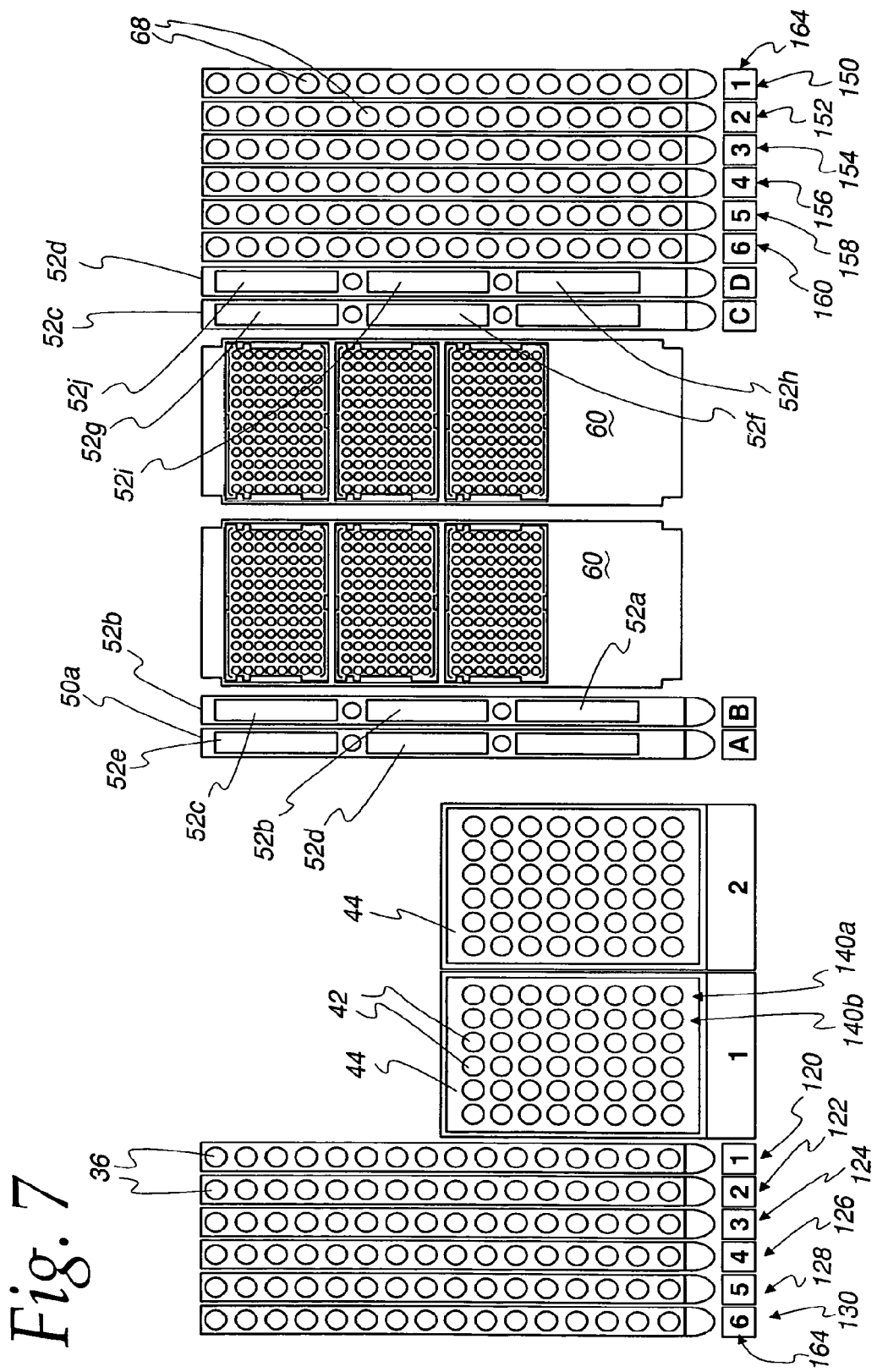
FIG. 7 is a simplified plan view of the deck of the testing device of FIG. 1.

Reference will now be had to FIG. 7 to generally explain an operation in which 96 samples are to be processed. While the head 30 is not shown in this view, it should be understood that it will travel over the components illustrated and lower pipettes 62 into tubes 36, 42, 68 and receptacles 52*a-j* to pick up fluids (i.e., specimen samples and reagents) and then move over the deck 22 to a different location over different tubes 42, 68 into which the picked up fluid is discharged.

For example, the head 30 would initially move over the pipette supply station 60 to pick up a set of eight pipettes 62 of the appropriate size, and then move to the first row 120 of specimen tubes to pick up eight specimen samples (e.g., from the last eight tubes [those in the top of FIG. 7] in row 120), and then move to the eight test tubes 42 located in row 140*a* at station 40*a*, where it discharges those specimen samples. Typically, some (e.g. six) of the first eight specimen samples would contain known materials so that the results of the analysis when processing is completed can be checked for accuracy.

The head 30 would then move over a discharge chute 146, where it would drop off the contaminated pipettes 62 (with the chute 146 open to a trash receptacle beneath the deck 22), and then proceed to the pipette supply station 60 for new pipettes 62, which it would then use to pick up eight specimen samples (e.g., from the other eight tubes in row 120) for transfer to the eight test tubes 42 located in row 140b at station 40a. This process would repeat for each set of eight specimens until all ninety-six test tubes 42 (in six rows 120, 122, 124, 126, 128, 130) have been provided with specimen samples.

At this point, the head 30 would be used to pick up an appropriate reagent from the appropriate receptacle 52a-j as required for the first step of processing, and then discharge that reagent into each of the various test tubes 42. With a head 30 having eight pipettes 62, such a process could involve up to twelve steps in picking up the first reagent.

Thereafter appropriate processing occurs at the processing station 40. This could involve, for example, using the transfer arms 46 to move the support brackets 44 between the different stations 40a-d for different steps of the process, with additional different reagents added at those different steps from the various receptacles 52a-j. At the completion of this processing, the item of interest (e.g., the isolated DNA) would be transferred by use of the head 30 and pipettes 62 to tubes 68 in trays 66 in rows (150, 152, 154, 156, 158, 160) which correspond to the tubes 36 in rows 120-130 which initially held the specimens.

As with the trays 50a-d for the receptacles 52a-j, the racks 34, 66 for the specimens may also be advantageously provided with icons thereon matching icons on the deck 22 to ensure that the racks 34, 66 are properly located on the deck 22. This enables the operator to reliably match the processed specimen sample in the tubes 68 in racks 66 with the specimens in the tubes 36 in the racks 34 and, in essence, allows the operator to reliably tell which processed sample is related to which specimen.

It should also be noted that in the above operation, the movement of the head 30 could be advantageously controlled so that it moves the pipettes 62 over and between the various tubes 36, 42 to minimize the possibility of contamination of specimen samples. That is, by supporting the pipettes 62 on the head 30 with a selected spacing matching that of the tube rows, the head 30 may be controlled to move so that when the pipettes 62 pass over a row of tubes 36, 42, they will be between the tubes 36, 42 as they do so. Moreover, with the pipettor spacing adjustable as previously noted, such an advantage may be obtained while at the same time allowing compact presentation of various components. For example, as can be seen in FIG. 7, the receptacles 52a-j and pipette supply station 60 can be arranged in significantly shorter row lengths than can the test tubes 42, thereby allowing each component to be provided so as to take up minimal space on the deck 22 notwithstanding relatively large space requirements for other components. For example, a test tube 42 can require more space than a stack of pipettes not only because it is relatively larger but also because processing on the deck 22 can require certain spacing between the tubes 42 which is not required for other components (e.g., reliably uniform heating of all tubes in a tube array may require that suitable heat sources [and space for those heat sources] be provided throughout a tube array, and sample processing components, such as magnets, may similarly need to be dispersed through a tube array). The spacing of the pipettors 32 may thus be advantageously adjusted to different uniform amounts, depending upon the component over which it is passing, to permit the supported pipettes to pass over and between the components, whatever the uniform spacing of the components, and thereby minimize the risk of contamination.

Figure 8:
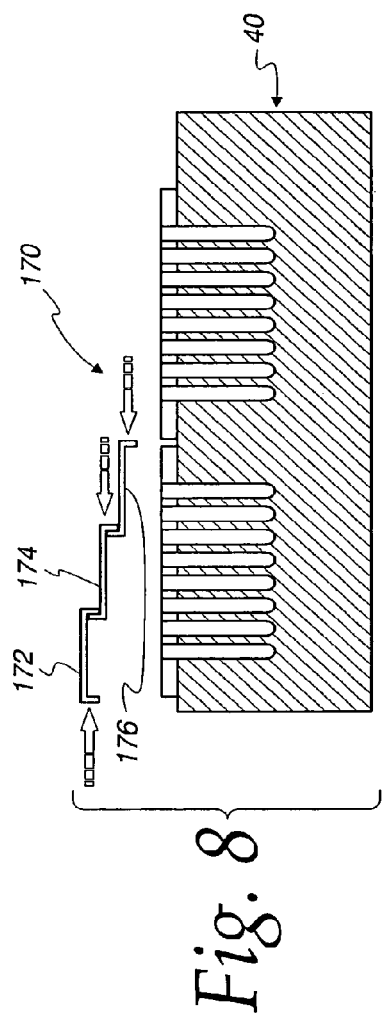
FIG. 8 is a simplified cross-sectional view illustrating a cover usable with a processing station of the FIG. 1 testing device in accordance with the present invention.

FIG. 8 illustrates an alternative embodiment which may be used separately from, or in conjunction with, the above described operation in which the pipettes 62 are moved between tubes 36, 42 as they pass thereover to prevent contamination. Specifically, an overlapping cover 170 may be provided above the tubes in the processing station 40, where the panels 172, 174, 176 of the cover 170 may be moved in the direction of the arrows to overlapping positions to uncover a particular row of tubes 42 into which the pipettes 62 are to discharge a fluid (sample or reagent), while keeping the remaining tubes 42 covered and thereby protected from possible contamination.

Figure 9:
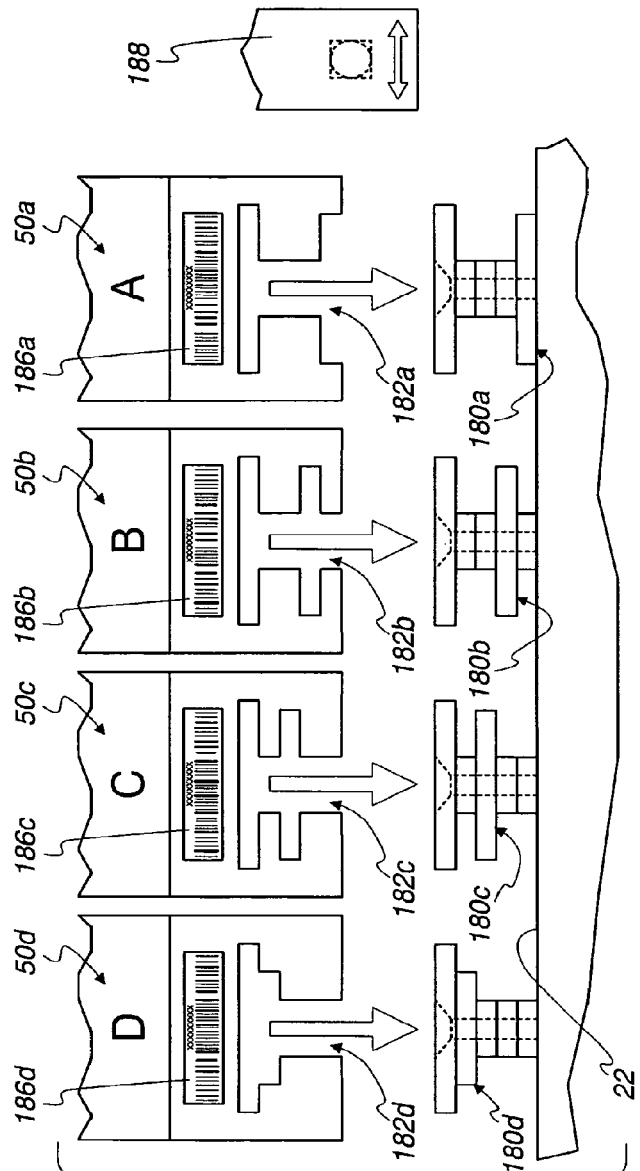
FIG. 9 is a partial view of the deck and trays of an alternative embodiment of an automated testing device incorporating the present invention.

FIG. 9 illustrates yet another alternative embodiment which may be used separately from or in conjunction with, the above described structure using icons 100-106 to ensure proper placement of the trays 50a-d on the deck 22. In this alternative, the deck 22 is provided with uniquely shaped pins 180a-d projecting therefrom at each location at which the trays 50a-d are to be positioned. The trays 50a-d are also provided with matching shaped slots 182a-d in the bottoms thereof whereby each tray 50a-d can only be secured at one position on the deck 22.

Still further, as also illustrated in FIG. 9, each tray 50a-d may also be provided with a suitable machine readable indicator 186a-d (such as a bar code) unique to each tray 50a-d, with a suitable reader 188 provided with the device 20, where the reader 188 scans the indicators 186a-d to verify proper positioning. The verification of the reader 188 could either be used to alert the operator to an error in loading the trays 50a-d, or could be used to adjust the controller for the head 30 to ensure that the head 30 goes to the proper receptacles 52a-j at the proper time during processing.

It should be understood that while the above description of FIG. 9 has been made in reference to the trays 50a-d having the reagent receptacles 52a-j, the same structure could also be used to ensure proper positioning of the specimen and processed sample racks 34, 66.

Figure 10A:
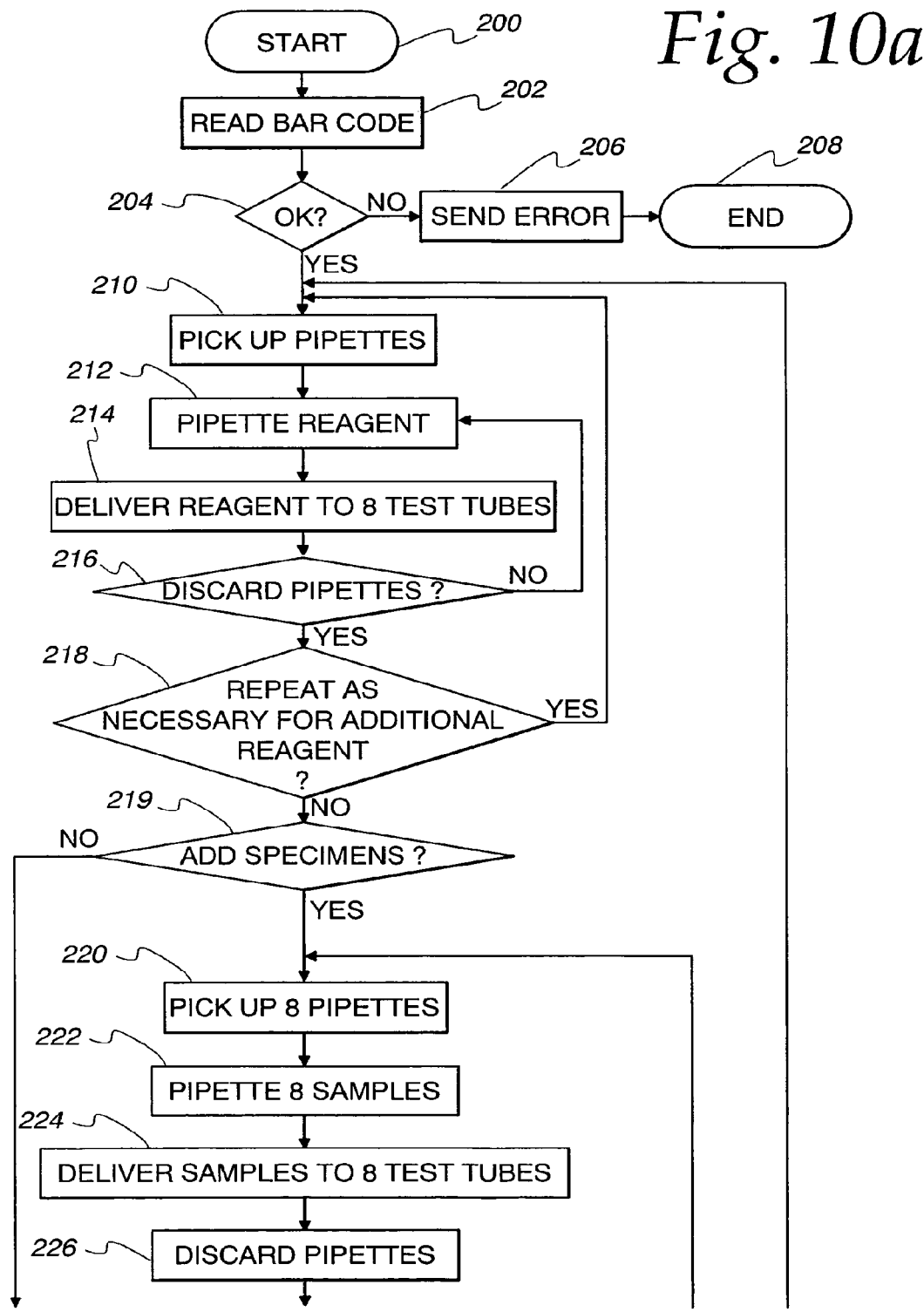
FIGS. 10a-10b is a flow chart of a process for using an automated testing device incorporating the present invention.
Figure 10B:
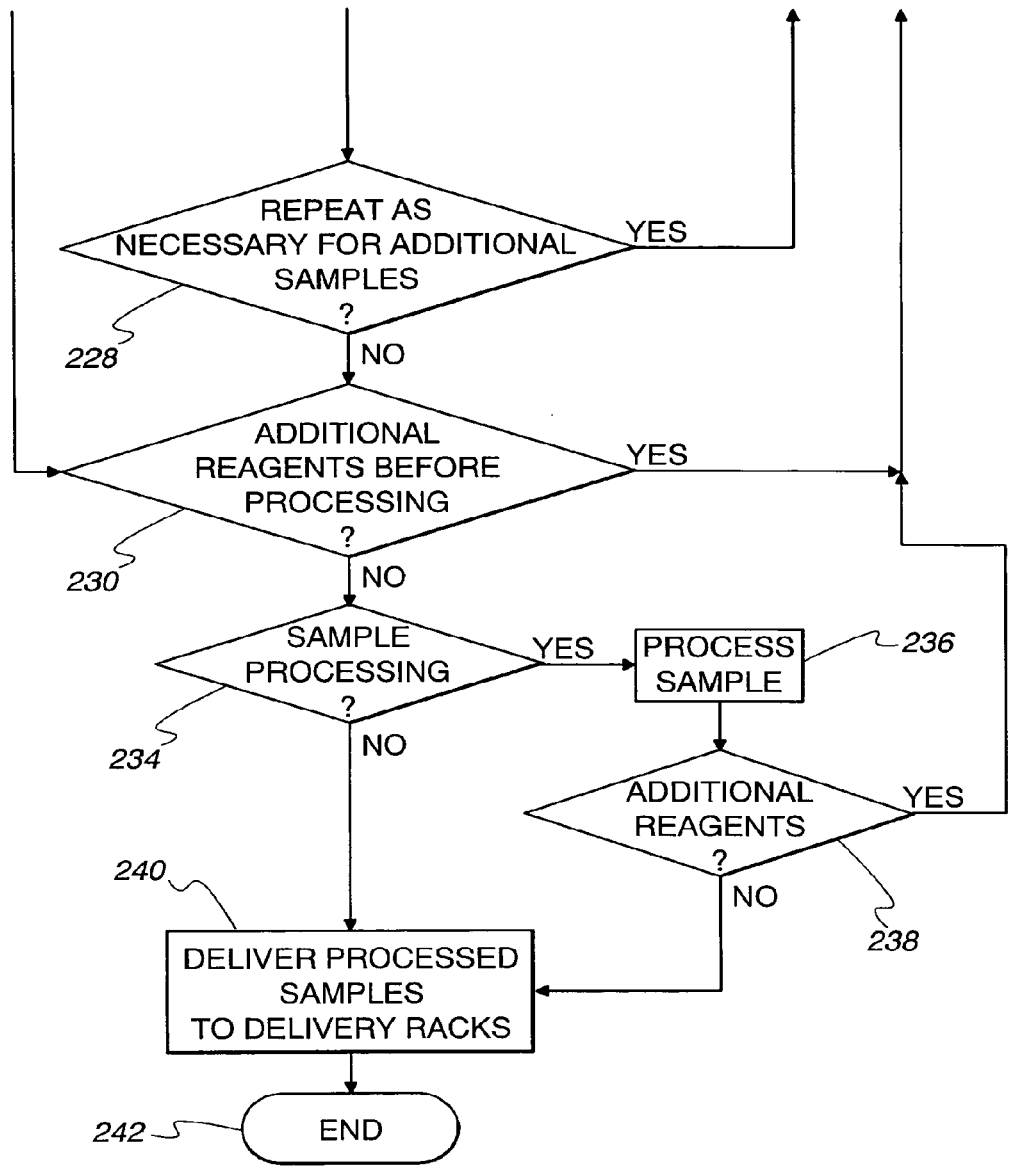

FIGS. 10a-10b illustrate the process of operating the device 20 such as previously described, but using a bar code reader 188 such as illustrated in FIG. 9. Prior to the start 200, the operator has already poured the various reagents from the containers 70-78 of the kit 80 into the various receptacles 52a-j, according to the number of specimen samples being processed, and reagent trays 50a-d and specimen and processed sample racks 34, 66 have been positioned on the deck 22 along with a suitable supply of pipettes.

After the operator suitably indicates to the device 20 that it may begin, the reader 188 at 202 reads the indicators 186a-d (e.g., bar codes) on the trays 50a-d (and racks 34, 66). If it detects at 204 that the trays 50a-d (and racks 34, 66) are not properly positioned, it sends an error message at 206 to the operator and stops operation 208 until the operator repositions the trays and racks to the proper position and starts again. If it detects at 204 that everything is positioned properly, operation continues with the head 30 moving at 210 to pick up eight pipettes 62, with the pipettes then moved at 212 to pick up a reagent from an appropriate receptacle 52a-j. The picked up reagent is then delivered at 214 to the test tubes 42.

The pipettes 62 may be discarded at 216 after only one use if contamination is a concern at that point, in which case steps 210-216 are repeated as necessary, as indicated at 218, until the first reagent has been loaded into all of the test tubes 42 which will receive specimen samples to be processed. Alternatively, if the reagent is to be added to more than eight test tubes 42 (e.g., to forty eight test tubes 42) where contamination with other materials is not a concern during that step, step 210 may be skipped and steps 212-216 repeated until it is determined that new the pipettes can/should be discarded, such as may occur when the first reagent has been added to all of the tubes 42 to be processed (e.g., six times for forty eight test tubes 42).

Once the first reagent has been loaded into all of the test tubes 42, steps 210-216 may further be repeated (as also indicated at 218) to add additional reagents to the test tubes 42 as desired. For example, uParticles may first be added to the tubes 42, and then Lysis buffer may be added. Of course, the reagents used may vary depending on the processing desired, and the present invention is not limited to use of any particular reagents.

If samples are to be added, as determined at 219, a similar process is then repeated at 220-228 wherein the samples are moved from eight sample containing tubes 36 to eight of the test tubes 42 for the first step of processing the samples, with those steps repeated at 228 until all of the specimen samples to be tested have been placed in test tubes 42. While the pipettes used to deliver specimen samples typically are required to be discarded after each use as at 226 to prevent contamination, it would be within the scope of the present invention to reuse pipettes if contamination does not necessitate using new pipettes (such as might occur, e.g., if additional quantities of the same specimen samples are to be delivered to the tubes 42 in more than one step).

If additional reagents are required after the specimen samples have been delivered to the test tubes 42 as determined at 230, operation returns to picking up pipettes at 210 for repetition of steps 210-218 as necessary. Once sufficient reagents have been added, operation then skips at 219 (since the samples have already been added at steps 220-228 and thus do not need to be added) to step 234 to determine whether processing should occur.

If sample processing is then ready to be done at 234, sample processing proceeds at 236. Any variety of process steps may be done at this stage, including washing, incubating and lysing, although again it should be understood that the present invention may be advantageously used irrespective of the particular processing being done on the samples.

If further sample processing is required at 238 using additional reagents, steps 210-236 are repeated to add those reagents and process the samples.

Once sample processing is completed as determined at 234, at 240 the pipettes 62 are used to deliver the processed samples to the tubes 68 in the racks 68, at which point (at 242) this phase of processing ends.

By adding the reagents to the test tubes 42 before the samples such as described in the above operation, the risk of contamination between samples may be minimized. However, it should be understood that the above operation is merely one example in which the present invention as disclosed herein may be used, and that variations on that operation may well be used within the scope of the invention. Therefore, it should be understood that the present invention could be advantageously used with, for example, a different order of adding reagents and samples (e.g., the samples could be added to the test tubes 42 before adding the reagents).

It should now be apparent from the above that the present invention may be used to ensure that samples and reagents may be properly handled by an operator of the testing device 20 with minimal risk of operator error, and may also be processed without serious risk of contamination of the samples.

Still other aspects, objects, and advantages of the present invention can be obtained from a study of the specification, the drawings, and the appended claims. It should be understood, however, that the present invention could be used in alternate forms where less than all of the objects and advantages of the present invention and preferred embodiment as described above would be obtained.

The invention claimed is:

1. A specimen handling system comprising:
   an instrument including
      a head adapted to carry selected fluids in X pipettes,
      a reagent receptacle adapted to permit entry of the X pipettes, and configured to be fillable by manual pouring of reagents into the receptacle,
      a processing station comprising a plurality of stations for processing a specimen to isolate a biological analyte of interest from the specimen; and
      a holder comprising an array of reaction vessels positioned in the holder, each reaction vessel adapted to receive specimens and reagents from the X pipettes, the holder adapted to be received by one of the plurality of stations at a time and transferred amongst and between the plurality of stations; and
   a reagent kit comprising a container, the container adapted to hold contents comprising a premeasured quantity of particles in a premeasured volume of fluid, wherein the particles have affinity for biological analytes of interest, the container adapted for pouring the contents into the reagent receptacle.

2. A method of detecting a biological analyte of interest, the method employing the system of claim 1, and comprising adding an internal control analyte to the contents of the container prior to pouring the contents of the container into the reagent receptacle.

3. The system of claim 1, further comprising a transfer arm for transferring the holder amongst the plurality of stations.

4. The system of claim 1, wherein the plurality of stations comprises a station for washing the specimen.

5. The system of claim 1, wherein the plurality of stations comprises a station for lysing the specimen.

6. The system of claim 1, wherein the plurality of stations comprises a station for heating the specimen.

7. The system of claim 1, wherein the plurality of stations comprises a station for cooling the specimen.

8. The system of claim 1, wherein the plurality of stations comprises a station for applying a magnetic field to the specimen.

* * * * *